United States Patent [19]
Isobe et al.

[11] Patent Number: 5,885,570
[45] Date of Patent: Mar. 23, 1999

[54] INDUCTION OF TOLERANCE WITH MODIFIED IMMUNOGENS

[75] Inventors: Mitsuaki Isobe, Winchester; Ban An Khaw, Milton, both of Mass.; Philip D. Nicol, Etobicoke, Canada

[73] Assignee: The General Hospital Corporation, Boston, Mass.

[21] Appl. No.: 644,377

[22] Filed: Jan. 23, 1991

[51] Int. Cl.⁶ .................................................. A01N 63/00
[52] U.S. Cl. ...................... 424/93.71; 424/88; 530/350
[58] Field of Search ................................ 424/88; 530/350

[56] References Cited

FOREIGN PATENT DOCUMENTS

| | | |
|---|---|---|
| 0 335 423 | 10/1989 | European Pat. Off. . |
| 0 352 761 | 1/1990 | European Pat. Off. . |
| WO 86/04145 | 7/1986 | WIPO . |

OTHER PUBLICATIONS

Rosenberg, et al., 1986. "Analysis of T–cell Subsets in . . . " Nature 322 : 829–831.

Eisai, K.K., Modified Streptokinase and its Preparation, *Patent Abstracts of Japan* 6 No. 214 (C–131) (1092) 27 Oct. 1982, JP–A–57 118 789.

Nordvall et al., *Allergy* 41(2):89–94 (1986), Abstract only.

Savoca et al., *Biochimica Biophysica Acta* 578(1):47–53 (1979), Abstract only.

Vik et al., *International Archives of Allergy and Applied Immunology* 74(1):55–62 (1984) Abstr. Only.

European Search Report for the corresponding European Application, EP 92 30 0503 filed Jan. 23, 1992.

Abuchowski, A. et al., *Journal of Biological Chemistry* 252(11):3578–3581 (1977).

Hall, B., *Transplantation Proceedings* 21(1):816–819 (1989).

Bach, F.H. et al., *New England Journal of Medicine* 317(8):489–492 (1987).

Bruce, M.G. et al., *Immunology* 57:627–630 (1986).

Cogswell, J.P. et al., *Cellular Immunology* 114:71–82 (1988).

Green, D.R. et al., *Immunity to Cancer* 2:245–258 (1989).

Nossal, G.J.V., *Transplantation Proceedings* 21(1):5–9 (1989).

Wie, S.I. et al., *Int. Archs Allergy Appl. Immun.* 64:84–99 (1981).

*Primary Examiner*—Lynette F. Smith
*Attorney, Agent, or Firm*—Sterne, Kessler, Goldstein & Fox P.L.L.C.

[57] ABSTRACT

A method is provided for inducing tolerance to T-cell mediated immunity. Particularly, tolerance is induced in a recipient mammal to a transplanted organ or tissue. Tolerance is induced by treating the recipient mammal with a MHC antigen which has been modified to render an immunosuppressive effect.

25 Claims, 3 Drawing Sheets

INDUCTION OF TOLERANCE WITH MODIFIED IMMUNOGENS

FIELD OF THE INVENTION

This invention is related to the use of modified transplantation antigens to induce tolerance to donor antigens in recipients of donor organs and tissues.

BACKGROUND OF THE INVENTION

To treat organ disease and organ failure, the use of allogeneic, or non-self, transplantation tissue has become increasingly important in medicine. The use of allografts, however, is limited by the frequent rejection of the graft tissue by the recipient host, because of antigenic differences between the donor and recipient.

The antigenic differences between individual members of the same species are referred to as "alloantigens." When alloantigens are involved in rejection of allogeneic tissue grafts, they are referred to as "histocompatibility antigens." The terms "major histocompatibility antigens" and "major histocompatibility complex" (MHC) refer to the products of a single closely linked region of genes.

These MHC gene products are displayed on cell surfaces and are an important barrier to successful allotransplantation. In humans, the MHC is, by international agreement, referred to as "HLA." The individual letters in this abbreviation have a variety of meanings, including "Human Leukocyte (or Lymphocyte) Antigen" and "Histocompatibility Locus Antigen." (Carpenter, C. B., in *Harrison's Principles of Internal Medicine*, ed. E. Braunwald et al., (McGraw-Hill, New York, 1987, page 337.)

Graft rejection is the consequence of an immune response to the histocompatibility antigens. Allografts generally survive for a period of days to weeks. However, they subsequently become inflamed and infiltrated with lymphocytes and monocytes, and the tissue eventually becomes necrotic. In the case of a skin graft, the grafted tissue is sloughed from the skin. However, in the case of a vital organ such as the heart, the sequelae of tissue rejection can be fatal to the recipient.

Following transplant into a human, a donor heart is closely monitored for signs of graft rejection. Most commonly, rejection is monitored by biopsying the donor heart tissue. A recent study described the performance of endomyocardial biopsies on cardiac transplant recipients weekly for the first 8 weeks after transplant, every other week for the next 8 weeks, monthly for the next year, and every 3–4 months for the remainder of the patient's life. (Ahmed-Ansari, A. et al., *Transplantation* 45:972–978 (1988)).

The biopsied tissue is then studied histologically for indicia of tissue rejection. A grade of rejection is determined on the basis of the degree of infiltration by leukocytes. (Ahmed-Ansari et al., supra). It is believed that the infiltrating leukocytes become sensitized to MHC antigens expressed by the graft tissue.

Despite the recognition that the MHC plays a major role in the success or failure of graft survival in a host mammal, current attempts to prolong graft survival have not exploited this knowledge. The most common method of prolonging graft survival is the administration of nonspecific immunosuppressive agents such as cyclosporine or cyclosporin AR and steroids. By suppressing the recipient's general immune response, survival of the graft can be enhanced. However, long-term use of immunosuppressive agents is associated with lowered resistance of the recipient to bacterial and viral infections. Furthermore, there is evidence that cancer incidence is increased in individuals such as kidney-transplant recipients, who have been treated long-term with immunosuppressive agents.

Experimental alternatives to non-specific immunosuppression of the transplant recipient have been studied. In mouse model systems, it has been shown that culturing allograft tissue before transplantation can lead to permanent acceptance of the tissue by the recipient. (Lafferty, K. J. et al., *Transplantation* 22:233–234 (1976); Bowen, K. M. et al., *Lancet* 2:585–586 (1979)). Although the mechanism by which such culturing leads to graft acceptance is not clear, it has been suggested that such culturing leads to the elimination of dentritic cells and other antigen-presenting cells rich in class 2 antigen expression. (Bach, H. B. and Sachs, D. H., N. E. *J. of Medicine*, Aug. 20, 1987, 489–492).

In another method of inducing tolerance in an animal model, the recipient is first given total lymphoid radiation, followed by reconstitution of the marrow using mixed donor-recipient marrow. Prior to transplantation, the donor marrow is treated to remove T-cells, thus preventing graft-versus-host disease in the recipient. The recipient is then tolerant to donor grafts. (Ilstadt, S. T., *Nature* 307:168–170 (1984)). However, this technique is not applicable for clinical use, because of high dosage of whole body irradiation.

Recently, presensitization of recipients with MHC class 1 antigen which present on allograft cells is shown to have antigen-specific immunosuppressive effects against allograft cells.

Despite the significant advances in understanding the MHC, a need exists for an improved method of inducing graft tolerance in mammalian recipients, especially humans.

SUMMARY OF THE INVENTION

Compositions and methods are provided for modulation of the immune response. The compositions comprise immunogens which are modified to render an immunosuppressive effect. That is, the modified immunogens are capable of modifying the immune response such that subsequent contact by similar immunogens does not illicit the immune response. The compositions and methods find use in inducing tolerance to immunogens, particularly immunogens involved in transplantation rejection, allergies, autoimmune diseases and the like.

DETAILED DESCRIPTION OF THE INVENTION

Figure 1:
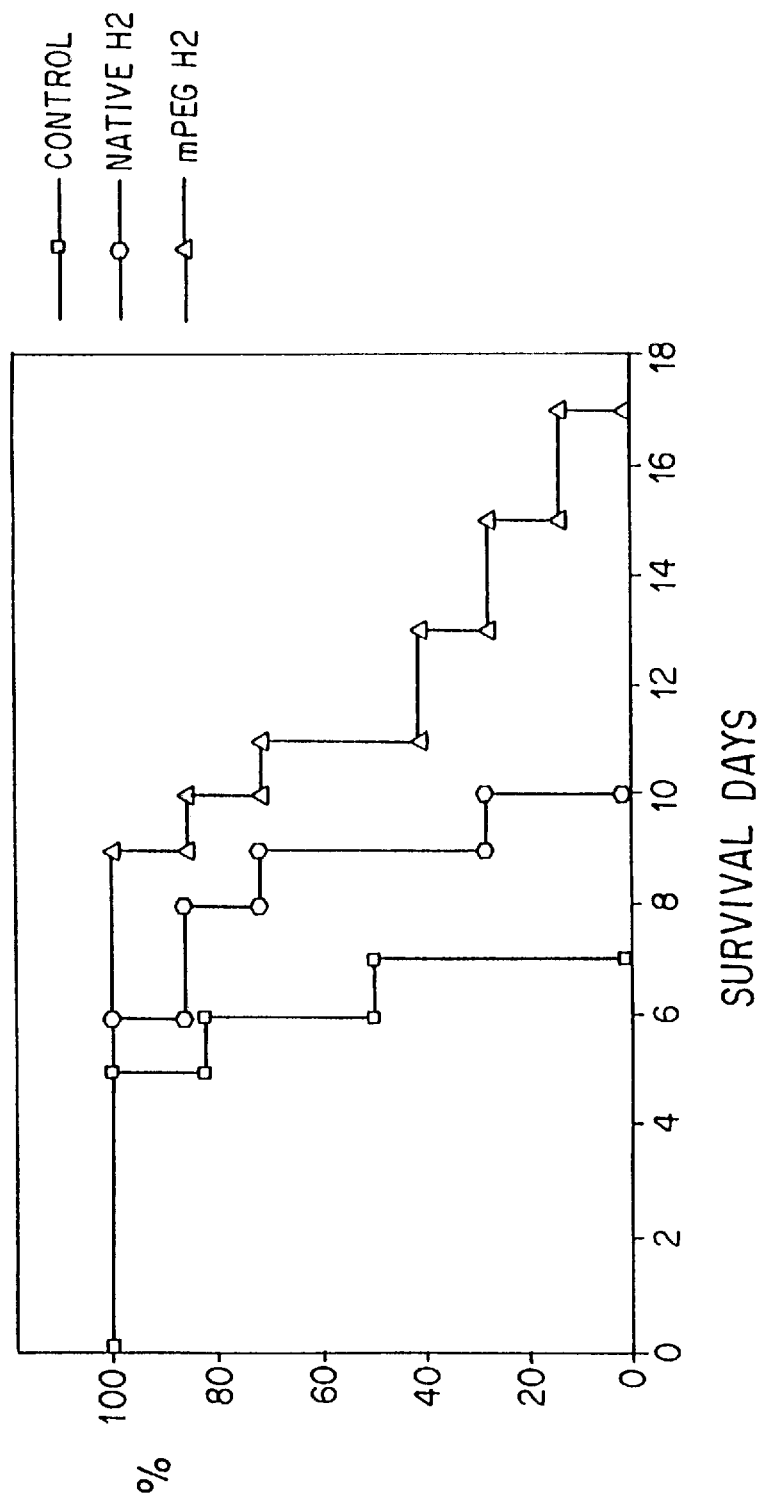
FIG. 1. Survival rate of the transplanted heart was plotted against days post transplantation. Allografts transplanted into mPEG modified H2K$^k$ antigen-immunized mice showed significant elongation of survival over allografts transplanted into either native H2K$^k$ antigen-immunized or normal control mice.

The present invention is drawn to compositions and methods for altering T-cell mediated immunity. Specifically, immunogens which are capable of eliciting a T-cell response have been modified to induce tolerance. The immunogens are modified by the attachment of a non-immunogenic polymer to available groups on the immunogen.

The term "mammal" is meant to include both human and non-human mammals.

The term "immunogen" means generally a protein or non-protein substance which is capable of eliciting an immune response in a mammal exposed to that substance. Thus, the term encompasses antigens and other factors which induce an immune response. For the most part, the term refers to immunogens capable of eliciting T-cell mediated immunity. Thus, the term includes components of the major histocompatibility complex, or immunogenic fragments thereof.

The term "modified" as used herein in reference to an immunogen means the complexing of one or more chemical groups to the antigen. The modification renders the antigen non-immunogenic or reduces the immunogenicity of the antigen.

The term "non-immunogenic" as used herein in reference to an immunogen or a modified immunogen means that a mammal does not raise an immune response upon exposure to the immunogen or modified immunogen, or to an organ or tissue expressing the immunogen.

The term "inducing tolerance" means exposing the mammal to an immunogen that has been modified to render it non-immunogenic or to reduce its immunogenicity. The immune system of the mammal does not raise an immune response against the antigen upon subsequent exposure of the mammal to that immunogen or to an organ or tissue expressing that immunogen.

The non-immunogenic polymer is selected from compounds which are linear, uncharged, pharmaceutically acceptable and render the immunogen non-immunogenic. For the most part, the polymers are selected from the methoxypolyethylene glycols, with the general structure $CH_3(OCH_2CH_2)_nOH$. Physical and chemical properties of the polyethylene glycols can be found in Bailey et al. (1986) in *Nonionic Surfactants* (Schick, M. J., Ed.) pp. 794–821, Marcel Dekker, Inc., New York.

As indicated, the non-immunogenic polymer, particularly monomethoxypolyethylene glycol (mPEG), is attached to the immunogen. Methods are available for attachment of the polymer to immunogens. One method is the use of cyanuric acid as a coupling agent, as described in Abuchowski et al., *J. Biol. Chem.* 252:3578–3581 (1977). See also, Jackson et al., *Analytical Biochemistry* 165:114–127 (1987) and Wilkinson et al., *J. of Immunol.* 139:326–331 (1987). The polymer can also be linked to the immunogen by the use of bifunctional agents, such as N-hydroxysuccinimide, to use as cross-linking agents (Buckamann et al., *Makromol. Chem.* 182:1379 (1982)). The mixed anhydride method can be utilized as disclosed by Wie et al., *Immun.* 64:84–99 (1981). Also, the PEG can be coupled to the $\epsilon$-amino groups of lysyn residues of the immunogen using 2-chloro-4-hydroxy-6-PEG-triazine as taught by King et al., *Arch. Biochem. Biophys.* 178:442–450 (1977).

Polymers of mPEG are available over a large range of molecular weights. For the most part, any molecular weight PEG can be utilized. However, it is recognized that there is an inverse relationship between the molecular weight of mPEGs and the degree of substitution. That is, when utilizing smaller molecular weight PEG polymers more attachment is needed to the immunogen than when larger molecular weight PEGs are utilized. Thus, varying degrees of substitution, i.e., the number of mPEG molecules attached per protein molecule, may be varied depending upon the immunogen and as indicated upon the molecular weight of the PEG utilized. The important concept is that as immunogens are converted to toleragenic products with concomitant reduction or total loss of allergenicity, the effect can be achieved with a lower degree of substitution by coupling mPEGs of increasing molecular weights. For the most part, longer reaction times coupled with higher concentrations of PEG to immunogen will increase the substitution or attachment of PEG molecules.

Generally, the PEG will be attached at a substitution of about 20% to about 80%, more generally about 40% to about 70% of the immunogen.

The modified immunogens of the present invention can be administered parentally by injection, rapid infusion, nasopharyngeal absorption (intranasopharyngeally), derma absorption, or orally. The compositions may alternatively be administered intramuscularly, or intravenously. Compositions for parenteral administration includes sterile aqueous or nonaqueous solutions, suspensions, and emulsions. Examples of nonaqueous solvents are polypropylene glycol, polyethylene glycol, vegetable oils such as olive oil, and injectable organic esters such as ethyloleate. Carriers or occlusive dressings can be used to increase skin permeability and enhance antigen absorption.

An important characteristic of immunologically-mediated organ and tissue rejection responses is the presence of leukocyte infiltrates in the transplanted tissue. Leukocytes are white blood cells that are capable of mediating a range of immunological effects. It is believed that many of the leukocytes present in the transplanted tissue are sensitized against antigens expressed by the donor transplanted tissue. Following activation, these leukocytes induce cytocidal effects against cells of the transplanted tissue. Through these observations, it is generally believed that T-cell mediated immunity plays a crucial role in the pathogenesis of rejection.

The antigens against which many of the leukocytes are sensitized are components of the major histocompatibility complex (MHC). Thus, a fundamental link in the rejection process is the expression of MHC antigens by the transplanted tissue. For example, in a heart transplant, it is generally believed that the vascular endothelial cells and passenger cells (such as macrophages and dendritic cells) of the graft express low levels of certain MHC antigens. These antigens may cause the initial sensitization of host lymphoid cells. (Ahmed-Ansari, A. et al., *Transplantation* 45:972–978 (1988)).

In one study, attachment of PEG to bovine serum albumin (PEG-BSA) caused the BSA to become non-immunogenic. Rabbits immunized with PEG-BSA did not raise antibodies to either PEG-BSA or native BSA. Furthermore, the PEG-BSA complex did not react with antibodies raised against native BSA. (Abuchowski et al., supra).

In mice, tolerance to human monoclonal IgG was induced by complexing the IgG with monomethoxypolyethylene glycol (mPEG). (Wilkinson, et al.,*J. Immunol.* 139:326–331

(1987)). Several enzymes, including arginase, catalase, and adenosine deaminase, have been rendered non-immunogenic by attachment of PEG. (Davis, S. et al., *Clin. Exp. Immunol.* 46:649–652 (1981); Saroca, K. V. et al., *Biochem. Biophvs. Acta* 578:47–53 (1979); Abuchowski, A. et al., *J. Biol. Chem.* 252:3582–3586)).

In general, immune reaction is categorized into two, B-cell immunity or humoral immunity and T-cell immunity or cell-mediated immunity. In B-cell immunity, antibodies produced by B cells and compliments play a major role for eliminating foreign antigens from the circulation. In contrast, in T-cell mediated immunity, cytotoxic T cells destroy target cells or virus. Allograft cells are shown to be destroyed through the T cell mediated immunity. It is of worthy to notice that tolerization using mPEG has proved and applied only for soluble antigens, i.e. for B-cell mediated immunity. In view of the significant difference in the mechanism between B-cell mediated and T cell mediated immunity, applicability of mPEG tolerization to T cell mediated immunity had yet to be established. Actually, until the present disclosure no attempt has been devoted for mPEG tolerization for immunological disorders concerning T cell immunity.

The MHC of the mouse has been studied extensively, primarily because highly inbred strains of mice (genetically identical individuals) are available. The mouse MHC, designated histocompatibility-2 (H2), is homologous to the MHC complex of humans, HLA. In both species the antigens of the MHC play a similar role in allowing the immune system to distinguish between self and non-self cells and tissues.

Human and mouse MHC antigens are divided into two classes, class I and class II, on the basis of functional differences. Human and mouse class I MHC molecules share about 70 to 75 percent of their amino acids (J. Klein, Immunology (John Wiley & Sons, 1982), p. 295).

Because the HLA and H-2 antigens play homologous roles within the immune systems of, respectively, humans and mice, the H-2 complex has long been used as a model system for studying the MHC in general. Work performed using inbred strains of mice has greatly advanced the ability to understand mechanisms of tissue rejection in humans. Thus, experimental results of transplantation studies in mice have immediate and direct applicability to human organ and tissue transplants.

According to the present invention, tolerance to graft tissue may be achieved by exposing the host mammal to a purified and modified MHC antigen expressed by the donor tissue. Although the invention is not bound by a particular mechanism of tolerance, it is possible that tolerance is achieved by preventing the initial sensitization of host lymphoid cells to antigens of the graft tissue and/or by preventing recognition of the graft antigens by the sensitized lymphocytes. Alternatively, the modified immunogens may serve to delete the T-cell subpopulation which recognizes the immunogen.

One embodiment of the present invention is to prevent allograft rejection. Thus, prior to transplant, the recipient (host) is exposed to modified MHC antigens of the type expressed by the donor tissue particularly modified MHC class 1 antigens. The host may also be treated with the modified antigens one or more times following transplant of the donor organ or tissue into the host. Alternatively, modified MHC antigens are administered to the recipient immediately after transplant.

Several methods are available for preparing proteins carrying MHC antigenic determinants. For example, cells may be solubilized with a detergent such as Triton X-100, which preserves the tertiary and quaternary structure of the MHC molecules. The solution is then subjected to ultracentrifugation, and the resulting supernatant contains MHC molecules and other proteins. The methods for isolation of the antigens are known in the art. See, generally, Mescher et al. in Methods in Enzymology. Langone et al. ed., pp. 86–109, Academic Press, NY (1983) and the references cited therein.

The purified donor antigens may be modified with any pharmaceutically acceptable chemical moiety that renders the antigens non-immunogenic.

In a preferred embodiment, the antigens are modified with monomethoxypolyethylene glycol (mPEG). Polymers of mPEG are available over a large range of molecular weights. The molecular weight of the mPEG utilized is selected based upon the immunogen and the method of linkage. As indicated earlier, when larger molecular weight molecules are utilized less substitution of the immunogen is needed.

Covalent attachment of the mPEG to the antigens may be accomplished by methods known in the art. While any of the methods disclosed earlier may be used, a disulfide linkage is preferred.

Activated PEG may be prepared by adding PEG to a solution of cyanuric acid in benzene, to which anhydrous sodium carbonate has been added. The solution is filtered, and petroleum ether is added. The precipitate is collected and redissolved in benzene. The precipitation and filtration processes are repeated several times until the petroleum ether is free of residual cyanuric chloride as determined by HPLC and detection with an ultraviolet detector. Alternatively, commercially activated mPEG may be utilized.

The activated PEG is then attached to the donor antigens. The antigens are dissolved in sodium tetraborate, the solution is brought to 4 degrees, and activated PEG is added. The pH is maintained at 9.2, and after 1 hour, unattached PEG is removed in an ultrafiltration cell.

The optimal molar ratio of PEG to antigen will depend upon the number of free amino groups in the antigen. Treatment of protein with activated PEG-5000 in molar amounts equal to 0.1, 0.25, 0.5, 0.75 and 1.0 of the available amino groups results in products with 5, 17, 32 and 42% of the amino groups substituted with PEG-5000.

As noted earlier, the percent of amino groups that are substituted will depend in part on the molecular weight of PEG that is used. In a preferred embodiment, from about 30 to about 60% of the amino groups of the antigen will be substituted with PEG of molecular weight ca. 5000.

The modified antigens may be introduced into the recipient using conventional methods for administering vaccines, including subcutaneous administration, intravenous administration, or injection.

The modified antigens are provided at therapeutically effective amounts. That is, in amounts sufficient to reduce or suppress the immunogenicity of the particular antigen or immunogen. The rates may vary depending upon the particular immunogen or the mode of administration. Generally, however, the modified antigens may be provided at rates ranging from about 10 ng of protein to about 1000 $\mu$g protein. See Experimental Section for more details.

It is recognized that the modified immunogens of the invention can be utilized to induce tolerance to any immunogen, particularly any immunogen which induces a T-cell mediated response. For example, the method can be utilized to suppress autoimmune disease, inflammation, or other T-cell mediated responses.

For autoimmune diseases, immunogens are selected from those which activate the T-cell response, for example, collagen for rhematoid arthritis and thyroglobulin for thyroiditis.

It may also be possible to utilize PEG coated antibodies to particular T-cell haplotypes to prevent these T-cells from mediating an immune response. The modified antibodies would have the same effect as modified immunogens in inducing tolerance.

The above disclosure generally describes the present invention. A more complete understanding can be obtained by reference to the following specific examples which are provided herein for purposes of illustration only, and are not intended to be limiting unless otherwise specified.

EXPERIMENTAL

Induction of Tolerance with Modified Immunogens

Materials and Methods

Mice: Inbred Balb/c ($H_2^d$) and C3H/He ($H2^k$) mice were purchased from Charles-River (Boston, Mass.). AKR ($H2^k$) mice were obtained from the Jackson Laboratory (Bar Harbor, Me.). Reagents, cell lines and antibodies: Monomethoxy polyethylene glycol (MW ca. 5000) activated with cyanuric chloride was obtained from Sigma (St. Louis, Mo.).

Hybridoma (11-4.1)[1] purchased from ATCC (Rockville, Md.) was grown as ascites tumors in pristane-primed Balb/c mice to produce anti-mouse $H2K^k$ monoclonal antibody. The monoclonal immunoglobulins were purified by protein A affinity column chromatography (Pharmacia, Piscataway, N.J.).

RDM-4 cell line was utilized. (Stallcup et al., *J. Immunol.* 127:923–930 (1981) Herrmann et al., *Proc. Natl. Acad. Sci. USA* 78:2488–2492 (1981)).

Cells were cultured growing in RPMI 1640 medium supplemented with 10% fetal calf serum and 0.1% gentamycin. For $H2K^k$ production, RDM-4 cells were grown in AKR mice as ascites tumors as described by Herzenberg et al., *Curr. Top. Microbiol. Immuno.* 81: 115–129 (1978).

Purification of $H2K^k$ antigen: $H2K^k$ antigen was purified according to the methods of Mescher et al., Methods in Enzymology, Langone JJ and Vunakis HV eds, pp86–109. Academic Press New York (1983) with some modification. The monoclonal antibody (11-4.1) was coupled with Sepharose 4B which had been activated with cyanogen bromide. $10^{10}$ washed RDM-4 cells were suspended at 4° C. in 20 ml of 10% Triton-x 100, 50 mM sodium phosphate, pH 7.2, containing 0.5mM phenylmethylsulfonyl fluoride (Sigma). The suspension was mixed for 20 minutes and then centrifuged for 10 minutes at 3600 g to pellet the nuclei. The supernatant was centrifuged for 1 hour at 100,000 g. The equal amount of 0.5% Triton-X 100, 5 mM sodium phosphate, pH 7.2 was added to the supernatant of this spin, and passed through a 0.45 $\mu$m filter. This sample was applied to a 5 ml precolumn of Sepharose 4B and then passed over the 11-4.1 column at 20 ml/hour. After washing the column with 0.5% Triton-X 100, 80 mM NaCl, 20 mM $NaHCO_3$, pH 8.3, $H2K^k$ was eluted with 0.5% deoxycholate, 130 mM NaCl, 20 mM $NaHCO_3$, pH 8.2. $NaDodSO_4$ polyacrylamide gel electrophoresis of eluates revealed only the expected heavy chain (47K) and β2-micro-globulin (12.5K). HPLC (C-8 Analytical Column, Beckman, Fullerton, Calif.) analysis of the eluates showed the purity of more than 95%. Purified $H2K^k$ was concentrated to about 200 $\mu$g/ml with Diaflo concentrator (Amicon, Danvers, Mass.), dialyzed against phosphate buffered saline, passed through a 0.45 $\mu$m filter then stored at −70° C. The protein concentration was determined by the method of Lowry et al., *J. Biol. Chem.* 193: 265–275 (1951) using bovine albumin as standard protein.

Modification of $H2K^k$ antigen: Purified $H2K^k$ antigen was modified with cyanuric chloride-activated monomethoxy poly-ethylene glycol. Approximately 500 $\mu$g of $H2K^k$ was mixed, volumetrically at 5:1 ratio, with 0.1M sodium tetraborate, pH 9.2. The solution was brought to 4° C. and activated with monomethoxy polyethylene glycol in an amount in 10-fold molar excess of available amino groups, assuming $H2K^k$ has 13 free amino groups. Reaction was carried out for 30 minutes on ice and then 30 minutes at room temperature. The sample was dialyzed against phosphate buffered saline. The modification was checked by $NaDodSO_4$ polyacrylamide gel electrophoresis and quantified with the trinitrobenzene sulfonate method of Habeeb AFSA, *Analytical Biochem.* 14:328–336 (1966). Modified $H2K^k$ showed an average of 60% reduction in primary amino groups.

Heart transplantation: Mice ectopic heart transplantation was performed using microsurgery technique.

Donor Preparation: Mice (15–25 g) were anesthetized with 3.6% chloral hydrate i.p. at a dose of 0.1 mL/10 g, and the abdominal skin was cleaned with 70% ethanol. The operation was performed under clean but nonsterile conditions. After a midline abdominal incision had been made and the abdominal aorta was cut to allow the animal to exsanguinate, the incision was extended cephalad to open the chest widely. The following procedures were performed under an operating microscope. The inferior vena cava was isolated and 0.5 to 1 mL of a cold, 7.5% solution of heparin in cardioplegia solution (7 g of glucose and 24 mEq of potassium chloride dissolved in 1 L of lactated Ringer's solution, pH 7.8 adjusted by Tris) was intermittently infused into the vessel with a 30 gauge needle. The inferior and superior vena cava were then ligated with 6-0 silk and cut away. The hili of the right and left lungs were ligated and transected independently and the aorta and pulmonary arteries were separated and cut with microscissors. A ligature was then placed around the mass of pulmonary veins. The heart, which was at that point detached from the chest wall, was placed in cold (4° C.) cardioplegia solution. The whole procedure was completed within 10 minutes.

Recipient preparation: The recipient mice were prepared as described above. The abdomen was shaved and a midline abdominal incision was made. The intestine was then exteriorized and wrapped with wet gauze. The abdominal aorta and inferior vena cava were gently separated below the branching of the renal vessels using cotton-tipped applicators and forceps. All small lumbar vessels were ligated with 6-0 silk. Proximal control of the inferior vena cava was obtained by ligature with 6-0 silk and the abdominal aorta was secured with a Yasargil artery clamp. Distal control was established en masse with 6-0 silk ligature. After closely adjacent venotomy and aortotomy were effected by microscissors, the donor heart was placed within the abdominal cavity. An end-to-side anastomosis was then made by running suture with 10-0 nylon strand (ETHILON) tipped with a BV75-3 needle. After the anastomoses had been completed, the distal and proximal ligatures and a clamp were loosened in this order slowly and carefully. At this point the grafted hearts became pink and began to contract within a few seconds of reperfusion, after which rhythmic contraction was restored. Warm saline was then dripped onto the graft. After the confirmation of continuous strong beats in the graft, the abdominal wall was closed with 6-0 silk. The animal was then warmed under a heat lamp. The ischemic time was defined as the interval between the injection of cardioplegia solution into the donor heart and reperfusion.

Balb/c mice were used as recipients and C3H/He mice were used as donors. Rejection was assessed with daily palpation of the grafts made by independent two observers who were blinded to the treatment. Complete cessation of the graft beat was defined as rejection. The observation was verified with gross inspection and histopathology of the excised graft.

Presensitization of animals with allogeneic proteins: Animals were subcutaneously injected with 50 $\mu$g of either native H2K$^k$ or mPEG modified H2K$^k$ antigen 7 days before transplantation. Control mice were injected with saline. Second injections were made on the day of transplantation. Each mouse was injected with 50 $\mu$g of either native or mPEG modified antigen, or saline.

Mixed lymphocyte reaction: Balb/c mice were injected subcutaneously with 50 $\mu$g of either native H2K$^k$ or mPEG modified H2K$^k$ antigen. 0.5 ml of saline was injected in control mice. Seven days after the injection, splenocytes were obtained from a pool of two animals per group. After washing, cells were resuspended in complete medium and cultured at a concentration of $5 \times 10^6$ cells/ml together with the same concentration of mitomycin C treated C3H/He stimulating spleen cells in a total volume of 200 $\mu$l. Each culture was performed in triplicate in flat-bottomed microculture plates (Falcon 3072, Beckton Dickinson, Lincoln Park, N.J.) and maintained in a humidified atmosphere at 5% $CO_2$ at 37° C. The cultures were harvested at 96 hours after a 16-hour pulse with 0.4 $\mu$Ci/well of $^3$H-TdR by using an automatic cell harvester (PHD285 Cambridge Technology, Cambridge, Mass.) onto glass fiber filters. Radioactivity was determined by liquid scintillation counter. Results were calculated from uptake of $^3$H-TdR and expressed as the mean uptake in cpm±SEM of triplicated samples.

Cytotoxic T lymphocytes assay: Presensitized Balb/c mice cells were mixed cultured with C3H/He mice stimulator cells in the same manner as described above. Cells were counted and cytolytic activity was tested by incubating them with $^{51}$Cr-labeled RDM-4 cells for 4-hour at 37° C. The percent specific release was calculated as: 100(a-b/t-b), where a is experimental release, b is spontaneous release, and t is total release, measured by adding 100 $\mu$l of 0.05% Nonidet P-40 to target cells. All cultures were performed in a total volume of 200 $\mu$l and in triplicate.

Results and Discussion

Heart transplantation: As shown in FIG. 1, C3H/He allografts were rejected at 6.6±0.2 days in saline-injected mice, 8.7±0.5 days in native H2K$^k$-injected mice, and 12.3±1.1 days in mPEG H2K$^k$-injected mice. There were statistical differences among them. Mice sensitized with mPEG-H2K$^k$ (10 $\mu$g) on the day of transplantation also showed greater survival of the graft (11.4±2.2, n=5). This immunosuppression could be transferred by mPEG-H2K$^k$-presensitized Balb/c spleen cells injected into recipient mice immediately after transplantation (11.5±1.8, n=7, p<0.001 vs. control).

The results in the in vivo study show that native class 1 H2 antigen has immunosuppressive effects on allograft cells which bear the same H2 antigen. Although some investigations have shown that presensitization with donor class 1 H2 antigen is immunosuppressive, none of those studies has proved the effects of purified H2 antigen. Important observation in the in vivo study is that presensitization with mPEG modified H2 antigen shows further immunosuppressive effects relative to native antigen presensitization. Because there is complete H2 disparity between Balb/c and C3H/He, the allograft will eventually be rejected even if tolerance against H2K is achieved.

Figure 2:
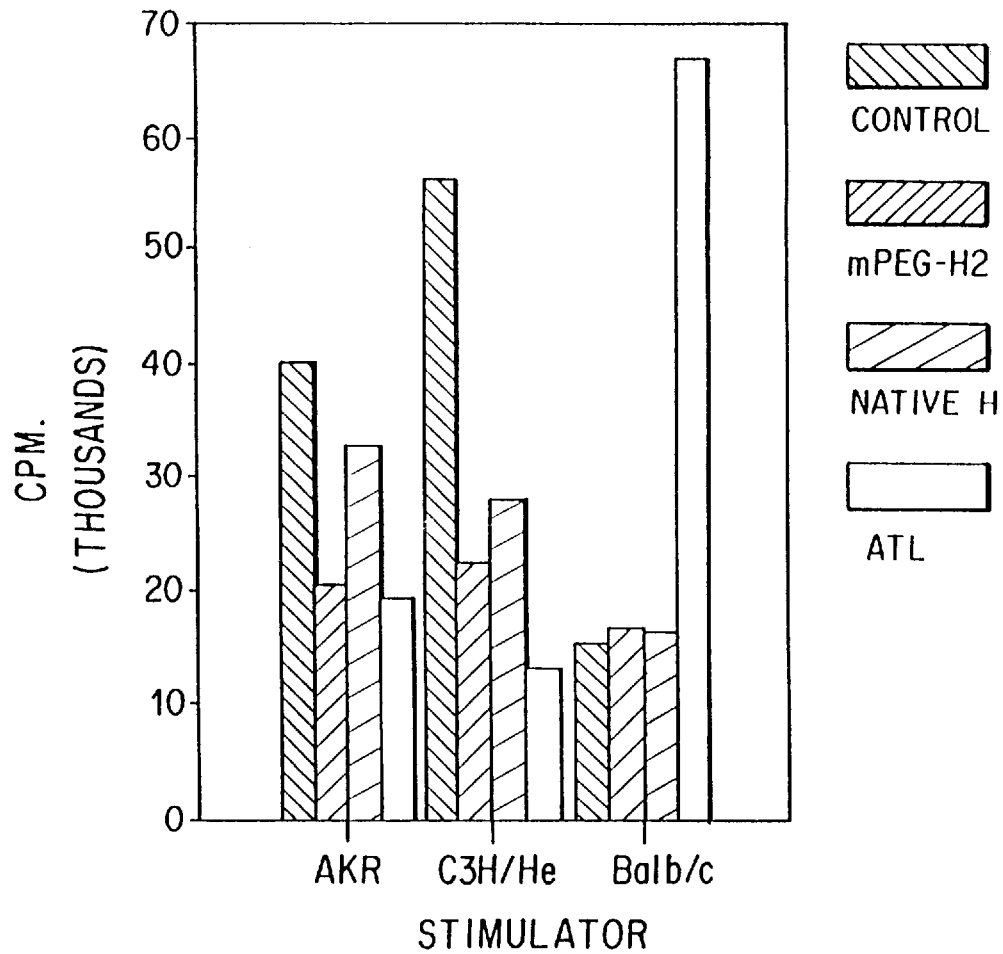
FIG. 2. $^3$H uptake of mixed lymphocyte culture cells. Control, native H2K$^k$-immunized or mPEG H2K$^k$-immunized Balb/c mice spleen cells were co-cultured with AKR (H2$^k$), C3H (H2$^k$) or Balb/c (H2$^d$) spleen cells (stimulator cells). A striking suppression of thymidine incorporation is noted in mPEG H2K$^k$ treated Balb/c mice spleen cells.

Mixed lymphocyte culture: The results of mixed lymphocyte culture were listed in FIG. 2.

The striking feature of these results are that there is strong suppression of thymidine uptake in mPEG modified H2 antigen presensitized Balb/c spleen cells. This finding supports the idea that T cell immunity is involved in the immune suppression observed in the in vivo study.

Figure 3:
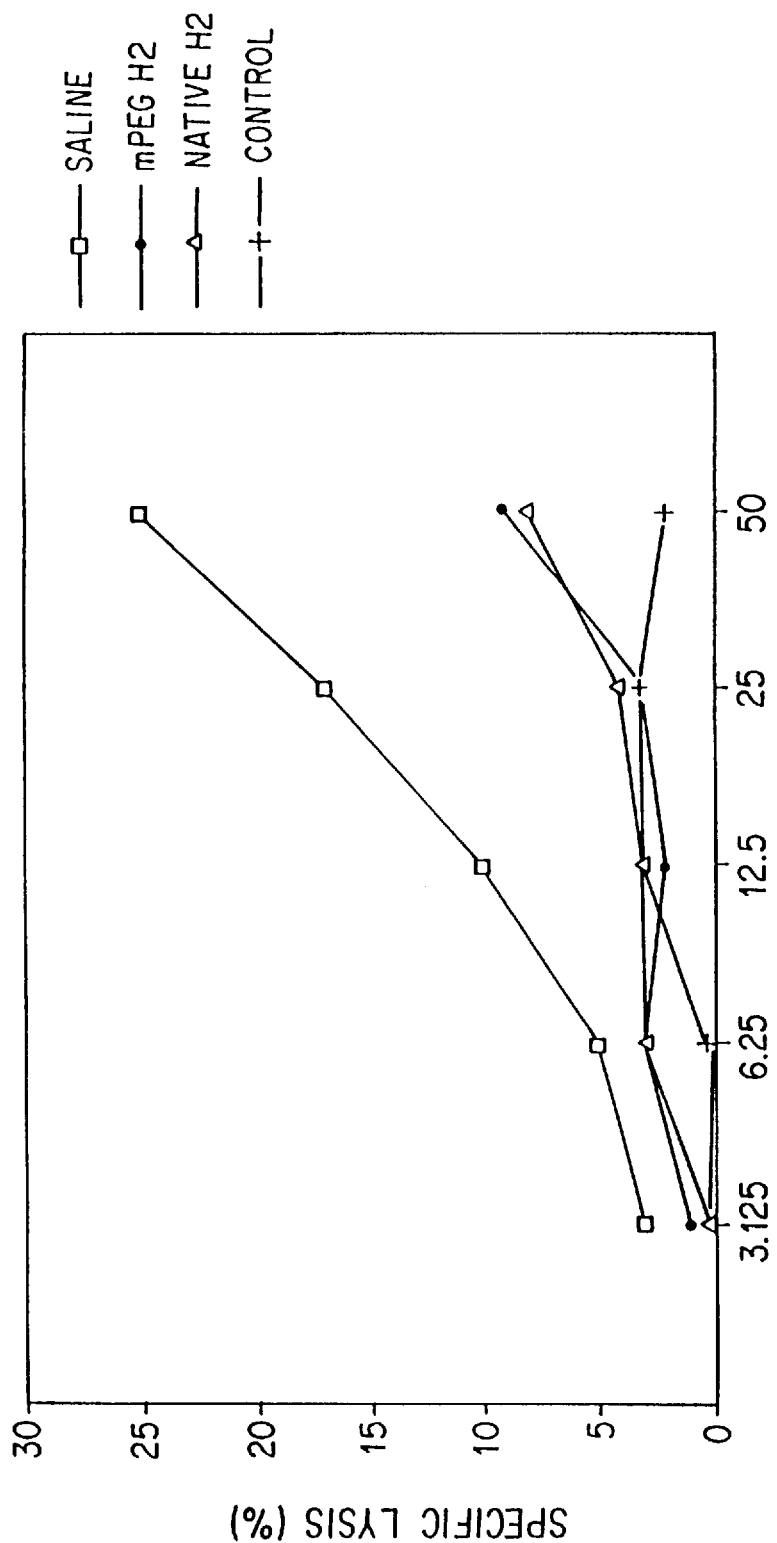
FIG. 3. Control, native H2K$^k$-immunized or mPEG H2K$^k$-immunized Balb/c spleen cells are co-cultured with C3H mice spleen cells for 4 days. Cytotoxic activity of these cells was tested by specific lysis of $^{51}$Cr labeled RDM-4 cells (H2$^k$). A suppression of cytotoxic activity is noted in mPEG H2K$^k$ or native H2K$^k$-immunized spleen cells. Cytotoxic activity of Balb/c spleen cells with syngeneic stimulation served as controls.

Cytotoxic T lymphocyte assay: The results of cytotoxic T lymphocyte assay are shown in FIG. 3.

These results also support the idea that T cell tolerization could be the cause of immune suppression observed in the in vivo study. These results show that effector rim of rejection is suppressed in mPEG-modified H2 antigen-presensitized mice spleen cells.

In summary, our data show that sensitization with mPEG modified H2 antigen induces tolerance, which allows an elongation of allograft survival. Tolerance also can be induced by the injection after the transplantation. Although tolerization of various antigens by mPEG modification has reported, all studies are concerned with humoral antigens. The fact that the technique shown in this study could be applied to T cell immunity leads to the application of this tolerization technique not only to the treatment of organ rejection, but also to the treatment of various kinds of diseases which involve T cell immunity.

Modifications of the above described modes for carrying out the invention that are obvious to persons of skill in medicine, immunology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

We claim:

1. A method of inducing tolerance to an immunogenic transplantation antigen, said method comprising:
   (a) administering to a mammal a composition comprising a therapeutically effective amount of an antigen which is modified to be non-immunogenic and corresponds to said immunogenic transplantation antigen; and
   (b) administering said immunogenic transplantation antigen.

2. The method of claim 1 wherein said immunogenic transplantation antigen and said modified corresponding antigen each comprises a component of the major histocompatibility complex.

3. The method of claim 1 wherein said modified corresponding antigen is modified to be non-immunogenic with monomethoxypolyethylene glycol.

4. A method of preventing rejection of transplanted donor tissue expressing an immunogenic antigen in a mammal receiving said donor tissue wherein said method comprises:
   (a) administering to said mammal a composition comprising a donor tissue-specific antigen, wherein said donor tissue-specific antigen is modified to be non-immunogenic; and (b) transplanting said donor tissue expressing an immunogenic antigen into said mammal.

5. The method of claim 4 wherein said composition is administered prior to transplantation of said donor tissue into said mammal.

6. The method of claim 4 wherein said composition is administered after transplantation of said donor tissue into said mammal.

7. The method of claim 4 wherein said composition is administered prior to and after transplantation of said donor tissue into said mammal.

8. The method of claim 4, wherein said modified donor tissue-specific antigen is an antigen of the major histocompatibility complex.

9. The method of claim 4 wherein said modified donor tissue-specific antigen is modified with monomethoxypolyethylene glycol.

10. A composition for inducing tolerance to T-cell mediated immunity, said composition comprising at least one immunogen which is capable of inducing a T-cell response wherein said immunogen is modified to render an immunosuppressive effect.

11. The composition of claim 10 wherein said immunogen is an antigen of the major histocompatibility complex.

12. The composition of claim 10 wherein said immunogen is modified with monomethoxypolyethylene glycol.

13. A method of increasing survival time of an allograft expressing an immunogenic antigen in a mammal wherein said method comprises:

(a) treating said mammal with an antigen that is specific to said allograft, wherein said antigen is modified to be non-immunogenic; and (b) transplanting said allograft expressing an immunogenic antigen into said mammal.

14. The method of claim 13, wherein said modified antigen specific to said allograft is modified with monomethoxylpolyethylene glycol.

15. The method of claim 1 wherein said immunogenic transplantation antigen and said modified corresponding antigen each comprises a major histocompatibility complex class 1 antigen.

16. The method of claim 4, wherein said donor tissue-specific antigen is a major histocompatibility complex class 1 antigen.

17. The method of claim 10 wherein said immunogen is a major histocompatibility complex class 1 antigen.

18. The method of claim 13, wherein said modified antigen comprises a major histocompatibility complex antigen.

19. The method of claim 18, wherein said modified antigen comprises a major histocompatibility complex class 1 antigen.

20. The method of claim 1, wherein step (a) precedes step (b).

21. The method of claim 1, wherein step (b) precedes step (a).

22. The method of claim 1, wherein steps (a) and (b) are simultaneous.

23. The method of claim 13, wherein step (a) precedes step (b).

24. The method of claim 13, wherein step (b) precedes step (a).

25. The method of claim 13, wherein steps (a) and (b) are simultaneous.

* * * * *